US011763921B2

(12) United States Patent
Wohlschlager et al.

(10) Patent No.: US 11,763,921 B2
(45) Date of Patent: Sep. 19, 2023

(54) ANNOTATING FETAL MONITORING DATA

(71) Applicant: KONINKLIJKE PHILIPS N.V., Eindhoven (NL)

(72) Inventors: Markus Wohlschlager, Sindelfingen (DE); Hansjoerg Geywitz, Kusterdingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 543 days.

(21) Appl. No.: 16/621,915

(22) PCT Filed: Jun. 18, 2018

(86) PCT No.: PCT/EP2018/066064
§ 371 (c)(1),
(2) Date: Dec. 12, 2019

(87) PCT Pub. No.: WO2018/229289
PCT Pub. Date: Dec. 20, 2018

(65) Prior Publication Data
US 2020/0121188 A1  Apr. 23, 2020

(30) Foreign Application Priority Data
Jun. 16, 2017 (EP) .................................. 17176293

(51) Int. Cl.
G16H 10/60 (2018.01)
A61B 5/00 (2006.01)
(Continued)

(52) U.S. Cl.
CPC ........... G16H 10/60 (2018.01); A61B 5/0011 (2013.01); A61B 5/4362 (2013.01);
(Continued)

(58) Field of Classification Search
None
See application file for complete search history.

(56) References Cited

U.S. PATENT DOCUMENTS 4,513,295 A * 4/1985 Jones ................. A61B 5/02411
346/33 ME
7,415,667 B2 * 8/2008 Rhodes .................. G06F 16/93
715/263
(Continued)

FOREIGN PATENT DOCUMENTS

JP 10171907 A 6/1998
JP 2002027176 A 1/2002
(Continued)

OTHER PUBLICATIONS

Huntleigh Healthcare Ltd., "With Dawes-Redman Trace Interpretation: Identifying and reducing risk throughout pregnancy—Advanced Fetal Monitoring Series", May 2017.
(Continued)

Primary Examiner — Christopher J Fibbi

(57) ABSTRACT

A computing device arrangement (20) for receiving fetal monitoring data from a fetal monitoring system is disclosed. The computing device arrangement comprises a display device (30) arranged to display the fetal monitoring data, a touchscreen device (32) and a processor arrangement (24) communicatively coupled to the display device and the touchscreen device. The processor arrangement is arranged to receive the fetal monitoring data from the fetal monitoring system, control the display device to display the fetal monitoring data, receive a freeform input (36) in a region of the touchscreen device from the touchscreen device; modify the fetal monitoring data by annotating a displayed region (34) of the fetal monitoring data with the freeform input, said displayed region corresponding to the region of the touchscreen device; and generate an output of the modified
(Continued)

fetal monitoring data for storage in a data storage device (28). Also disclosed are a fetal monitoring system including such a computing device arrangement and a method of generating freeform annotations with such a computing device arrangement.

12 Claims, 8 Drawing Sheets

(51) Int. Cl.
*A61B 8/00* (2006.01)
*G06F 3/04883* (2022.01)
*G16H 30/40* (2018.01)
*A61B 8/08* (2006.01)
*G06F 3/0354* (2013.01)
*H04W 12/06* (2021.01)
*H04W 12/08* (2021.01)
*G16H 40/63* (2018.01)

(52) U.S. Cl.
CPC .......... *A61B 5/7435* (2013.01); *A61B 5/7475* (2013.01); *A61B 8/0866* (2013.01); *A61B 8/468* (2013.01); *G06F 3/03545* (2013.01); *G06F 3/04883* (2013.01); *G16H 30/40* (2018.01); *H04W 12/06* (2013.01); *H04W 12/08* (2013.01); *A61B 5/4356* (2013.01); *G16H 40/63* (2018.01)

(56) References Cited

U.S. PATENT DOCUMENTS

| | | | | |
|---|---|---|---|---|
| 7,586,654 | B2* | 9/2009 | Hoberock | H04N 1/3871 |
| | | | | 358/444 |
| 8,730,243 | B2 | 5/2014 | Wenholz | |
| 2003/0004991 | A1* | 1/2003 | Keskar | G06V 30/1444 |
| | | | | 715/256 |
| 2006/0152516 | A1* | 7/2006 | Plummer | G16H 40/67 |
| | | | | 345/538 |
| 2009/0043195 | A1* | 2/2009 | Poland | A61B 8/465 |
| | | | | 600/437 |
| 2009/0327856 | A1 | 12/2009 | Mouilleseaux | |
| 2010/0235782 | A1* | 9/2010 | Powell | G16H 40/67 |
| | | | | 715/764 |
| 2011/0126127 | A1* | 5/2011 | Mariotti | H04M 7/0027 |
| | | | | 715/753 |
| 2011/0145274 | A1* | 6/2011 | Avinash | G16H 30/40 |
| | | | | 707/769 |
| 2012/0078647 | A1* | 3/2012 | Grassle | G16H 15/00 |
| | | | | 715/810 |
| 2013/0245463 | A1 | 9/2013 | Stuebe et al. | |
| 2014/0189560 | A1* | 7/2014 | Caspi | G16H 40/63 |
| | | | | 715/771 |
| 2014/0253467 | A1* | 9/2014 | Hicks | G06F 3/03545 |
| | | | | 345/173 |
| 2014/0292814 | A1 | 10/2014 | Tsujimoto | |
| 2015/0045641 | A1* | 2/2015 | Rule | A61B 5/742 |
| | | | | 600/347 |
| 2016/0321906 | A1 | 11/2016 | Whitney | |
| 2017/0006231 | A1* | 1/2017 | Mori | G11B 27/3027 |
| | | | | 705/30 |

FOREIGN PATENT DOCUMENTS

| | | |
|---|---|---|
| JP | 2010113504 A | 5/2010 |
| KR | 2003082028 A | 10/2003 |
| KR | 2011013939 A | 2/2011 |
| WO | 2017060791 A1 | 4/2017 |

OTHER PUBLICATIONS

Szcomen, "STAR5000Plus Fetal Monitor", Feb. 2017.
Gibbs, S., "Wacom Bamboo Spark review: pen and paper with digital tracks", Apr. 2016.
Kelion, L., "Lenovo Yoga Book copies handwriting off paper notepads", BBC, Technology Desk Editor, Aug. 2016.
Anonymous, "Radio-frequency identification", Wikipedia, Dec. 2015.
"Omniview-SisPorto", The Fetal Monitoring Central System with SisPorto Automated Analysis, Aug. 2016.
Sonicaid Fetalcare et al., "CTG Archiving & Reviewing Software", Dec. 2013, Huntleigh.
Apparent Apps B.V., "Partogram on the App Store", Jul. 2014, iTunes Preview.
Definition: "Free-Form text", Accessed Dec. 2019.
International Search Report and Written Opinion, International Application No. PCT/EP2018/066064, dated Sep. 10, 2018.

* cited by examiner

ANNOTATING FETAL MONITORING DATA

This application is the U.S. National Phase application under 35 U.S.C. § 371 of International Application No. PCT/EP2018/066064, filed on 18 Jun. 2018, which claims the benefit of European Application Serial No. 17176293.3, filed 16 Jun. 2017. These applications are hereby incorporated by reference herein.

FIELD OF THE INVENTION

The present invention relates to a computing device arrangement for receiving fetal monitoring data from a fetal monitoring system, the computing device arrangement comprising a display device arranged to display the fetal monitoring data and a processor arrangement arranged to control the display device.

The present invention further relates to a fetal monitoring system including such a computing device arrangement.

The present invention further relates to a computer-implemented method of annotating fetal monitoring data with such a computing device arrangement.

The present invention further relates to a computer program product for implementing such a method on a computing device arrangement.

BACKGROUND OF THE INVENTION

Fetal monitoring is commonly applied during the latter stages of pregnancy, for example to diagnose abnormal conditions such as fetal distress syndrome. This typically is achieved using cardiotocography in which a plurality of sensors applied to the abdomen of the pregnant woman is used to simultaneously measure the fetal heart rate and uterine contractions. This for example may be used to establish a relationship between the fetal heart rate and the uterine contractions, with changes in the relationship, e.g. changes in the fetal heart rate as a response to uterine contractions, potentially being indicative of the occurrence of such abnormal conditions. This allows medical professionals to timely intervene and reduce the risk of the well-being of the fetus being compromised.

The visualization of the sensor data including the fetal heart rate and uterine contractions traditionally is achieved using a thermal printer forming part of the fetal monitoring setup. The thermal printer typically produces a paper strip onto which the sensor data and associated parameters are recorded (printed), which has the advantage that a medical professional can manually annotate the paper strip to highlight key events during the fetal monitoring, e.g. during labour. Such manual annotation is highly desirable as it can be done in a straightforward and personalized manner, e.g. by means of handwriting, such that the annotations can be easily recognized at a later stage, e.g. during the evaluation of the fetal monitoring data post-birth.

A downside of such paper strips is that the paper strips can become quite long, for example during extended labour, which as is well-known per se can take well in excess of 24 hours. Consequently, large amounts of paper strips are produced during this period, which complicate evaluation of the fetal monitoring data at a later stage. Moreover, there may be a legal requirement to retain the fetal monitoring data after birth, for example as potential evidence in any legal disputes regarding the medical care received by the pregnant woman being monitored, such that large volumes of paper strips need to be stored or alternatively scanned to facilitate storage of the data in digital form. This is cumbersome, time-consuming and costly.

For this reason, fetal monitoring systems have emerged in which the fetal monitoring data is displayed on a portable display device such as a tablet, for example as disclosed in US 2012/0232398 A1, which discloses a wireless fetal and maternal monitoring system including a fetal sensor unit adapted to receive signals indicative of a fetal heartbeat. The system further includes a contraction actuator actuatable upon a maternal uterine contraction. A gateway device provides for data visualization and data securitization. The gateway device provides for remote transmission of information through a data communication network. A server adapted to receive the information from the gateway device serves to store and process the data, and an interface system to permits remote patient monitoring.

In such fetal monitoring systems, a user typically can insert annotations into the fetal monitoring data using drop-down menus or the like that can be activated by an appropriate user interface such as a touchscreen of the portable display device. It has been found that the typical users of such fetal monitoring systems find insertion of such annotations unsatisfactory due to the involved manner in which the annotations are to be inserted as well as the lack of personalized nature of the inserted annotations, which typically are represented in the digitized fetal monitoring data using a default font or the like. Moreover, in order to operate such drop-down menus or the like, the user typically needs to rely on user interfaces such as a keyboard or mouse, which are notoriously difficult to clean such that over time such user interfaces can become a health hazard to the mother and her unborn child being monitored in the vicinity of such user interfaces.

SUMMARY OF THE INVENTION

The present invention seeks to provide a computing device arrangement that offers a user of a fetal monitoring system a more flexible way of annotating digital fetal monitoring data.

The present invention further seeks to provide a fetal monitoring system including such a computing device arrangement.

The present invention further seeks to provide a computer-implemented method that offers a user of a fetal monitoring system a more flexible way of annotating digital fetal monitoring data.

The present invention further seeks to provide a computer program product for implementing such a method on a computing device arrangement.

According to an aspect, there is provided a computing device arrangement for receiving fetal monitoring data from a fetal monitoring system, the computing device arrangement comprising a display device arranged to display the fetal monitoring data; a touchscreen device; and a processor arrangement communicatively coupled to the display device and the touchscreen device, the processor arrangement being arranged to receive the fetal monitoring data from the fetal monitoring system; control the display device to display the fetal monitoring data; receive a freeform input in a region of the touchscreen device from the touchscreen device; modify the fetal monitoring data by annotating a displayed region of the fetal monitoring data with the freeform input, said displayed region corresponding to the region of the touchscreen device; and generate an output of the modified fetal monitoring data for storage in a data storage device. The freeform input comprises handwritten or drawn annotations, wherein the computing device arrangement further comprises identification means communicatively coupled to the processor arrangement, wherein the processor arrangement is arranged to receive identification data comprising user information identifying a user generating the freeform input from the identification means and to label at least some of said freeform annotations based on the identification data of the user generating the freeform input.

In accordance with embodiments of the present invention, a computing device arrangement is provided on which fetal monitoring data is displayed and can be annotated in a freeform manner, e.g. as handwriting or a drawing or the like, using a touchscreen associated with the display device, such that annotated fetal monitoring data can be generated in a digital format including freeform annotations, thereby avoiding the need to retain large strips of paper on which the fetal monitoring data is printed, whilst at the same time allowing the digital data to be annotated in essentially the same manner as such paper strips. In this manner, a user is provided with the intuitive annotation functionality of such paper strips without the need to generate or at least retain such paper strips.

In a preferred embodiment the identification means comprise an RF (radio frequency) tag reader or a finger print reader, wherein RF tag data received from the RF tag reader and finger print data received from the finger print reader comprise identification data.

In a preferred embodiment, the touchscreen device is a display screen of the display device, i.e. is integral to the display device such that the user can simply touch the display device in an area in which the user wishes to generate a freeform annotation. However, in an alternative embodiment the touchscreen device may be separate to the display device, e.g. may be a separate tablet or the like onto which the user can provide the freeform annotations. In such a scenario, the touchscreen region of the separate tablet or the like typically is mapped onto the display screen of the display device such that the user-generated freeform annotation in a region of the touchscreen of the tablet or the like is mapped to a corresponding region of the display screen of the display device.

In yet another embodiment, the computing device arrangement further comprises a printer device arranged to print the displayed fetal monitoring data from the fetal monitoring system on a printable medium, the printer device comprising an annotation region exposing a portion of the printable medium comprising the fetal monitoring data printed thereon, wherein the touchscreen device is a pressure-sensitive touchscreen device arranged in the annotation region underneath said portion of the printable medium. This has the advantage that the user can still write on the printable medium, e.g. on the paper strip, whilst the writing is recorded by the underlying touchscreen device and added as a freeform annotation to the digital representation of the fetal monitoring data. Such a printer device for example may be a thermal printer, although other printers such as an inkjet printer or laser printer may also be contemplated.

In a particularly advantageous embodiment, the computing device arrangement comprises an RF tag reader as the identification means communicatively coupled to the processor arrangement, wherein the processor arrangement is arranged to label at least some of said annotations based on RF tag data as identification data received from the RF tag reader, said RF tag data comprising user information for a user generating the freeform input. In this manner, the freeform annotations can be tagged with the user information, which for example may be used for the identification of the person generating a particular freeform annotation or in another example may be used to identify a user type, e.g. professional function or capacity, of that person.

Such a person may carry the RF tag on their body, e.g. in an identification badge or the like. In another advantageous embodiment, the computing device arrangement further comprises a plurality of styluses for generating the freeform input on the touchscreen device, each stylus comprising a RF tag programmable to contain said information. This has the advantage that the RF tag is guaranteed to be in close proximity to the touchscreen device, which preferably includes the RF tag reader such that when the user uses his or her stylus to generate a freeform annotation, the RF tag is guaranteed to be within communication range of the RF tag reader.

In yet another advantageous embodiment, the processor arrangement further is arranged to receive a user request for the retrieval of previously stored modified fetal monitoring data; retrieve the user-requested modified fetal monitoring data from the data storage device; and control the display device to display the retrieved modified fetal monitoring data, wherein each of the labelled annotations is displayed as a function of its label. For example, the processor arrangement further may be arranged to control the display device to display each labelled annotation in a colour indicative of a type of the user responsible for the generation of said annotation. This makes it straightforward for the user evaluating the retrieved fetal monitoring data to recognize who was responsible for the generation of a particular freeform annotation, e.g. a nurse, doctor, or the like, with different roles be represented by different colours.

In still another advantageous embodiment, the processor arrangement further is arranged to receive further identification data from the identification means, said further identification data identifying a user requesting the retrieval of previously stored modified fetal monitoring data; evaluate the further identification data to establish an authorisation level of the user requesting the retrieval of previously stored modified fetal monitoring data; and control the display device to display the retrieved modified fetal monitoring data, wherein only the annotations labelled based on the received identification data are displayed that the user requesting the retrieval of previously stored modified fetal monitoring data is authorised to see. In this embodiment, the user information attached to the freeform annotations as a label is used as an authorisation verification means such that a user evaluating stored fetal monitoring data will only see those freeform annotations that the user is authorised to see as determined from the further identification data associated with that user. This therefore can be used to prevent users evaluating previously stored fetal monitoring data from seeing all annotations in that data.

According to another aspect, there is provided a fetal monitoring system including at least one fetal monitoring sensor and the computing device arrangement of any of the herein described embodiments wherein the at least one fetal monitoring sensor is arranged to provide the processor arrangement with the fetal monitoring data. This therefore provides a self-contained fetal monitoring system in which freeform annotations can be generated within digitized fetal monitoring data as explained in more detail above.

According to yet another aspect, there is provided a computer-implemented method of annotating fetal monitoring data, the method comprising receiving the fetal monitoring data from a fetal monitoring system; displaying the fetal monitoring data on a display device; receiving a freeform input in a region of a touchscreen device from the touchscreen device, wherein the freeform input comprises handwritten or drawn annotations; modifying the fetal monitoring data by annotating a displayed region of the fetal monitoring data with the freeform input, said displayed region corresponding to the region of the touchscreen device; and generating an output of the modified fetal monitoring data for storage in a data storage device. With such a method, fetal monitoring data may be stored in a digitized form whilst still including freeform annotations, thereby combining the advantages of compact data storage of such digital data and intuitive annotation of the fetal monitoring data by a medical practitioner for example. The computer-implemented method further comprises receiving identification data comprising user information for a user generating the freeform input from an identification means, and labelling the freeform annotation based on said identification data.

In an embodiment, the computer-implemented method further comprises receiving an RF tag data or finger print data as identification data comprising user information for a user generating the freeform input from an RF tag reader or finger print reader; and labelling the annotation based on said RF tag data or finger print data such that each freeform annotation can be identified based on the RF tag data or finger print data with which the annotations are labelled.

Such labels may be used to control the manner in which the freeform annotations are displayed when retrieving previously generated fetal monitoring data from the data storage device. To this end, the computer-implemented method may further comprise receiving a user request for the retrieval of previously stored modified fetal monitoring data; retrieving the user-requested modified fetal monitoring data from the data storage device; and controlling the display device to display the retrieved modified fetal monitoring data, wherein each of the annotations labelled based on the received RF tag data or finger print data is displayed as a function of its label.

For example, displaying each of the annotations labelled based on the received RF tag data as a function of its label comprises controlling the display device to display each labelled annotation in a colour indicative of a type of the user responsible for the generation of said annotation such that the origin of such annotations can be immediately recognized from the colour in which they are displayed on the display device.

In another embodiment, the computer-implemented method further comprises receiving further identification data from the identification means, said further identification data identifying a user requesting the retrieval of previously stored modified fetal monitoring data; evaluating the further identification data to establish an authorization level of the user requesting the retrieval of previously stored modified fetal monitoring data; and wherein controlling the display device to display the retrieved modified fetal monitoring data comprises displaying only the labelled annotations that the user requesting the retrieval of previously stored modified fetal monitoring data is authorised to see. In this embodiment, a user unauthorised to see certain freeform annotations is prevented from seeing such annotations by the use of the labels attached to such annotations in the stored fetal monitoring data.

According to yet another aspect, there is provided a computer program product comprising a computer readable storage medium having computer readable program instructions embodied therewith for, when executed on a processor arrangement of the computing device arrangement of any of the herein described embodiments, cause the processor arrangement to implement the method of any of the herein described embodiments. Such a computer program product may be used to configure a computing device arrangement to implement various aspects of the present invention.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
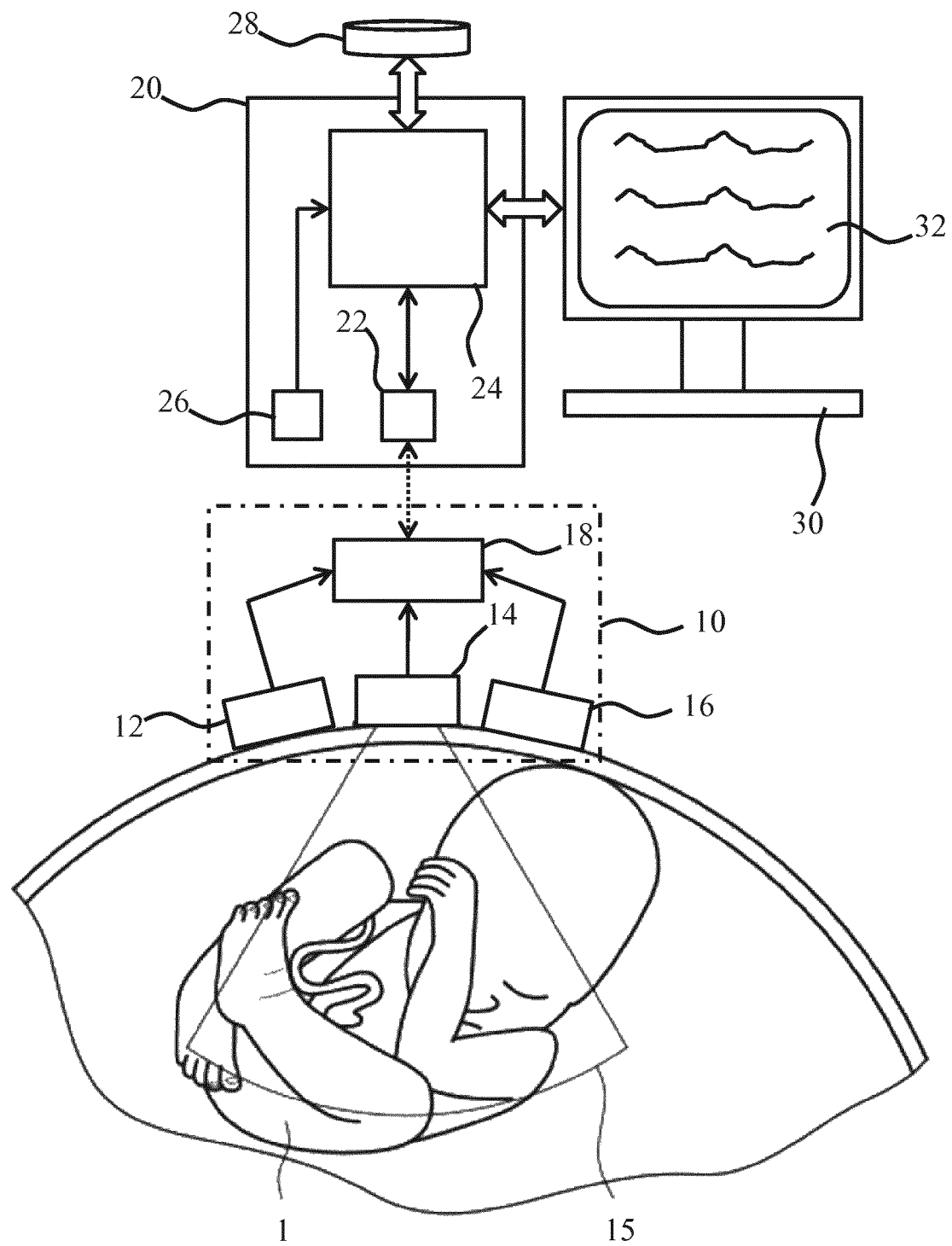
FIG. 1 schematically depicts a fetal monitoring system according to an embodiment of the present invention.

It should be understood that the Figures are merely schematic and are not drawn to scale. It should also be understood that the same reference numerals are used throughout the Figures to indicate the same or similar parts.

FIG. 1 schematically depicts a fetal monitoring system according to an example embodiment. The fetal monitoring system comprises a fetal monitoring arrangement 10 including a plurality of sensors 12, 14, 16 communicatively coupled to a communication module 18 arranged to communicate the sensor data of the sensors 12, 14, 16 to a communication module 22 of a base unit of a computing device arrangement 20. The plurality of sensors in an embodiment includes at least a toco sensor 12 and a fetal heartrate monitoring sensor 14 for monitoring the heartrate of the fetus 1, for instance using ultrasound waves 15. For example, the fetal heartrate monitoring sensor 14 may be a Doppler ultrasound sensor. The toco sensor 12 equally may be implemented in any suitable manner, for example using a strain gauge element, an accelerometer or the like to detect the contractions of the muscles around the mother's womb carrying the fetus 1. Optionally, the plurality of sensors may include one or more further sensors 16, which may be any suitable type of sensor such as for example a temperature sensor to sense the body temperature of the mother, and further useful types of sensors will be immediately apparent to the skilled person. The plurality of sensors may be attached to the pregnant mother's abdominal area in any suitable manner, for instance individually using an adhesive or alternative by integration in a belt or a strap or the like, which may be secured against the mother's abdomen in any suitable manner. As such sensor arrangements and their attachment to the mother's abdomen are well-known per se, this is not explained in further detail for the sake of brevity only.

The communication module 18 may be any suitable type of communication module, such as a communication module adapted for wired or wireless communication with the communication module 22 of the base unit of the computing device arrangement 20. Any suitable communication standard may be deployed between the communication modules 18 and 22. In case of a wireless communication standard, a low-energy wireless communication protocol such as Bluetooth is preferred to limit the exposure of the fetus 1 to the radio waves used for such wireless communication.

The base unit of the computing device arrangement 20 further comprises a processor arrangement 24 including one or more processors arranged to process the sensor signals received from the plurality of sensors and to control a display device 30 on which the processed sensor signals are displayed. The display device 30 may be integral to the base unit or alternatively may be a separate device communicatively coupled to the base unit in a wired or wireless fashion. Typically, the processor arrangement 24 is adapted to control the display device 30 such that in a first region, e.g. a first horizontal region, of the display device 30 the sensor signals from the toco sensor 12 are displayed and the sensor signals from the fetal heart rate monitoring sensor 14 are displayed in a second region, e.g. a second horizontal region, wherein the progress of these signals over time may be displayed in any suitable manner as is well-known per se. The simultaneous display of the sensor signals from the toco sensor 12 and from the fetal heart rate monitoring sensor 14 allows a medical practitioner such as a midwife, nurse or consultant to establish a correlation between these signals and to observe changes in such a correlation, e.g. changes in the heartrate of the fetus 1 detected with the fetal heart rate monitoring sensor 14 during labour as indicated by the contractions detected with the toco sensor 12, which changes may signal a health risk to the fetus 1 or another complication during labour, which may be acted upon by the medical professional, thereby reducing the risk of serious and/or irreversible health issues for the fetus 1.

Any suitable processor arrangement 24 may be used for this purpose. For example, the processor arrangement 24 may comprise one or more application-specific integrated circuits (ASICs) and/or one or more generic central processing units (CPUs) programmed to perform the functions described in the present application. The processor arrangement 24 may comprise a single processor or may comprise multiple processors such as a CPU and a graphics processing unit (GPU), wherein a first processor is a signal processor adapted to process the sensor signals from the fetal monitoring arrangement 10 and a second processor is communicatively coupled to the first processor and is arranged to control (communicate with) the display device 30.

The base unit of the computing device arrangement 20 equally may take any suitable form. For example, the base unit may be a personal computer, tablet computer, a dedicated bedside monitor, and so on.

As previously explained, a medical practitioner such as a midwife, nurse or consultant typically may wish to annotate the graphical representation of the sensor data, for example to explain certain changes in the data where such changes are caused by an external stimulus such as the administration of food, medication or the like or by a change in the physiological condition of the mother or fetus. Of course, other reasons for such a medical practitioner to annotate a particular incident within the sensor data may exist. Traditionally, where such a graphical representation of the sensor data was generated using a printer device such as a thermal printer, the medical professional would simply annotate the paper strip produced by such a printer device using a pen or pencil by writing on the paper strip. In contrast, where such a graphical representation of the sensor data was generated on a display device 30, the medical practitioner would be offered a graphical user interface, for example including drop-down menus or the like, through which the medical practitioner could select a particular annotation to be added to the digitized graphical representation of the sensor data using typical user interfaces such as a keyboard, mouse, trackball or the like, which annotation can be reproduced in a standardized form when printing the sensor data, e.g. in a defined location on the printout such as a predefined annotation area using a predefined font. This however is rather cumbersome and involved in particular during labour, where the medical practitioner will be focused on the delivery of the child, i.e. fetus 1, of the mother and will be reluctant to dedicate an inordinate amount of time on interacting with the computing device arrangement 20, specifically its user interfaces, in other to select the appropriate drop-down menus on the display device 30 to facilitate the addition of an annotation to the graphical representation of the sensor data, with a further disadvantage that such annotations typically are then represented by a standard font such that the medical practitioner loses the ability to annotate the graphical representation of the sensor data in his or her own handwriting. Moreover, the user interfaces required to provide such annotations, e.g. a keyboard and/or mouse, are easily contaminated with biological contaminations, e.g. bacteria or the like, and are difficult to effectively disinfect such that these user interfaces can become a health hazard to the pregnant woman and her unborn child, which of course is highly undesirable.

Figure 2:
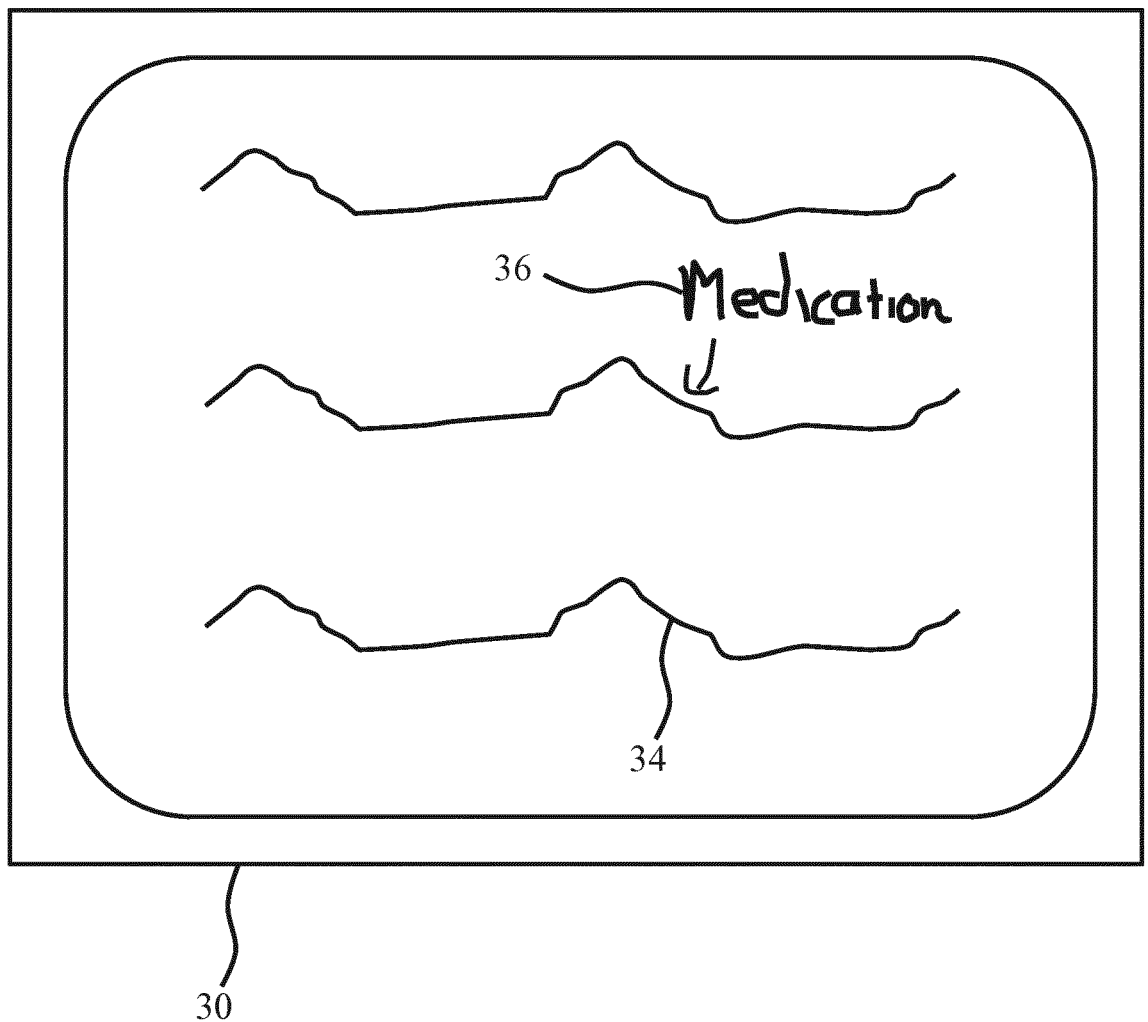
FIG. 2 schematically depicts an aspect of a computing device arrangement for use with a fetal monitoring system according to any embodiment of the present invention in more detail.

In accordance with the present invention, the computing device arrangement 20 further comprises a touchscreen 32 communicatively coupled to processor arrangement 24 onto which the medical professional can provide freeform annotations 36, i.e. handwritten or drawn annotations as schematically depicted in FIG. 2 by the handwritten annotation "Medication" and drawn arrow indicating a point in time or a particular change in the graphical representation 34 of the sensor data from the fetal monitoring arrangement 10. More particularly, the processor arrangement 24 is arranged to annotate the sensor data with the freeform annotations 36 as received from the touchscreen 32 such that the region of the touchscreen 32 in which the user, e.g. the medical professional, has generated the freeform annotation 36, is mapped onto a corresponding region of the display device 30 onto which the graphical representation 34 of the sensor data is displayed such that the appropriate portion of the sensor data is labelled with the freeform annotation 36. This has the further advantage that the equipment used to generate the freeform annotations 36 can be easily disinfected (cleaned), thereby greatly reducing the risk to the pregnant woman and her unborn child. In a straightforward embodiment, the touchscreen 32 forms an integral part of the display device 30 such that a user can simply touch the touchscreen 32 of the display device 30 to provide the freeform annotation 36 in the desired location, i.e. at the relevant portion of the sensor data are displayed on the display device 30.

Figure 3:
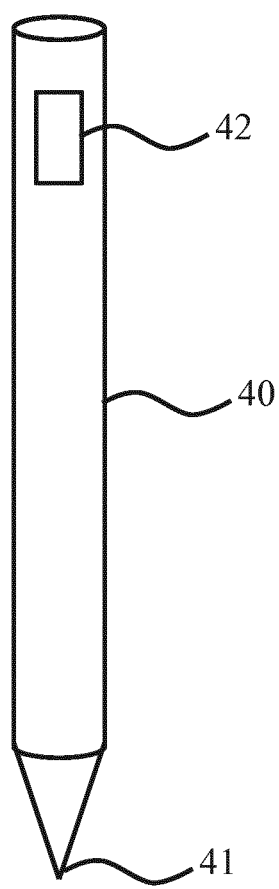
FIG. 3 schematically depicts an example embodiment of a stylus for use with such a computing device arrangement.

Any suitable type of touchscreen 32 may be used for this purpose. In some embodiments, the touchscreen 32 is a pressure sensitive touchscreen in which its user may generate a freeform annotation 36 by pressing down on the touchscreen 32 as is well-known per se although it should be understood that other types of touchscreens, e.g. capacitive touchscreens, may be used in any embodiment in which such other types of touchscreens facilitates the generation of such freeform annotations. The user may generate the freeform annotation 36 on the touchscreen 32 in any suitable manner. For example, the user may use his or her finger, a pen or the like. In an embodiment, the touchscreen 32 is provided with a dedicated stylus 40 as schematically depicted in FIG. 3, which dedicated stylus may be provided with a narrow tip 41 to allow its user to generate a freeform annotation 36 with a high degree of precision, thereby closely mimicking his or her handwriting or drawing style.

The processor arrangement 24 may be further adapted to store the sensor data modified with the freeform annotations 36 as received from the touchscreen 32 in a data storage device 28, e.g. for data retention purposes or to facilitate evaluation of the modified sensor data at a later point in time, e.g. post-birth. The data storage device 28 may be integral to the computing device arrangement 20 although in some embodiments the data storage device 28 may comprise a remote data storage arrangement accessible to the computing device arrangement 20 over a network, e.g. a private network such as a local area network (LAN) of a medical facility in which the mother is giving birth. Such a remote data storage arrangement may be located on-site or off-site, e.g. in the form of cloud storage. In case of such a remote data storage arrangement, the processor arrangement 24 may be adapted to communicate with the remote data storage arrangement through the data communication module 22 or another data communication module of the computing device arrangement 20, e.g. a network adapter or the like. Any suitable type of data storage devices or combination thereof may be used for such data storage, e.g. optical disks, magnetic disks, memory devices, and so on.

In a preferred embodiment, the processor arrangement is adapted to label each freeform annotation 36 with user information of the user generating the freeform annotation, e.g. user identity, professional capacity or function of the user, and so on. Such user information may be incorporated in the freeform annotation 36 in any suitable manner, e.g. as metadata. To this end, the computing device arrangement 20 further comprises a RF tag reader 26 communicatively coupled to the processor arrangement 24, which RF tag reader 26 may be integrated in any suitable entity of the computing device arrangement 20 such as its base unit, the display device 30 or the touchscreen 32. The RF tag reader 26 is arranged to read an RF tag 42 carried by the user and containing the user information to be read out from the RF tag 42 by the RF tag reader 26, with the RF tag reader 26 communicating the read out user information to the processor arrangement 24 for storage as a label to the freeform annotation 36 generated by that user with the touchscreen 32. The RF tag reader 26 may deploy any suitable communication technology such as near field communication to extract the user information from the RF tag 42. The user may carry the RF tag 42 in any suitable manner, such as for example in the form of a chip in an identification badge or the like. However, in a particularly advantage embodiment the computing device arrangement 20 comprises a plurality of styluses 40, with each stylus 40 comprising an RF tag 42 programmable to contain the user information of a particular user of the fetal monitoring system such that the user may be automatically identified by the system upon providing a freeform annotation 36 with his or her stylus 40 on the touchscreen 32. In order to ensure reliable communication between the RF tag 42 and the RF tag reader 26 in this embodiment, the RF tag reader 26 preferably is integrated into touchscreen 32.

Figure 4:
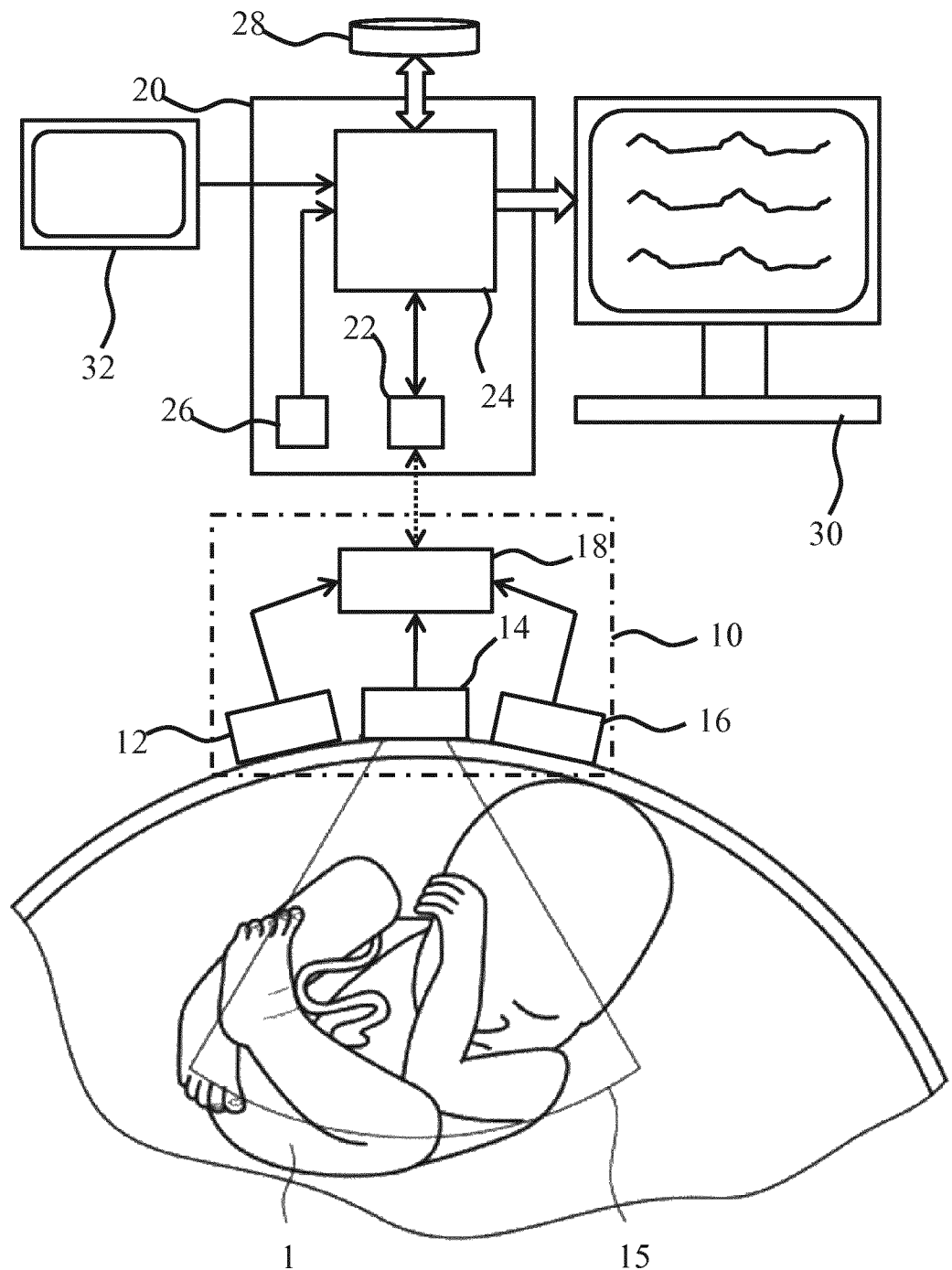
FIG. 4 schematically depicts a fetal monitoring system according to another embodiment of the present invention.

In the embodiments described above, the touchscreen 32 forms part of the display device 30. However, it should be understood that embodiments of the present invention are not limited to such an integral arrangement of the touchscreen 32 within the display device 30. FIG. 4 schematically depicts an alternative embodiment in which a separate touchscreen 32 is provided, e.g. a customised touchpad having an impressed or engraved reference to the sensor data displayed on the display device 30 or on a paper strip printed by a thermal printer such as an impressed or engraved reference grid of the sensor data. Although this requires the medical professional to look at the sensor data at a different device, it has the advantage that the medical professional is more mobile and can generate the freeform annotations 36 is a more flexible manner as the touchscreen 32 is decoupled from the display device 30.

Figure 5:
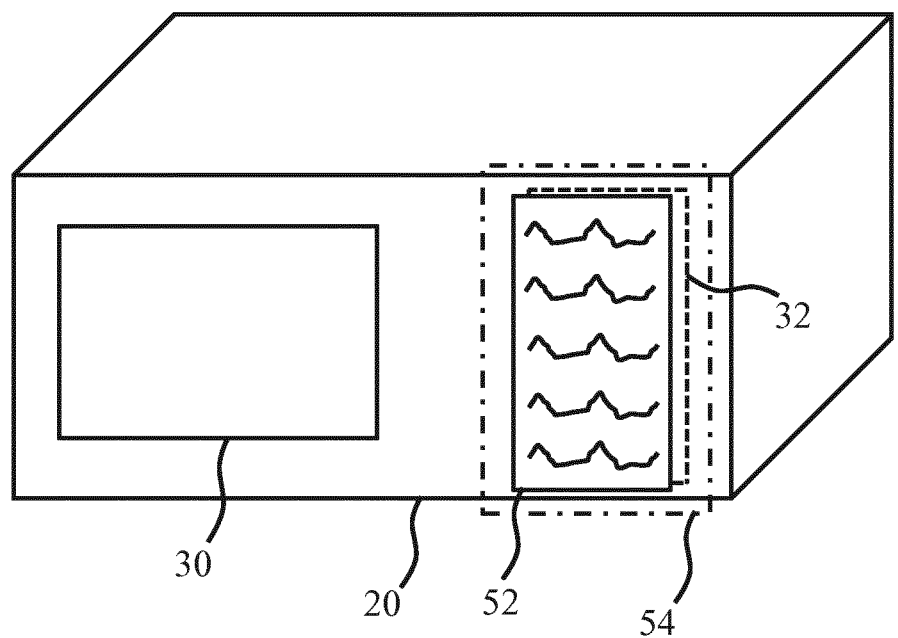
FIG. 5 schematically depicts another aspect of a computing device arrangement for use with a fetal monitoring system according to any embodiment of the present invention in more detail.

In another embodiment, the computing device arrangement 20 comprises a printer device 50 as schematically depicted in FIG. 5, such as a thermal printer device or alternatively an inkjet printer or a laser printer. The printer device 50 is arranged to print the displayed fetal monitoring data from the fetal monitoring system on a printable medium 52, e.g. a paper strip or the like. The printer device comprises an annotation region 54 exposing a portion of the printable medium 52 comprising the fetal monitoring data printed thereon, wherein a pressure-sensitive touchscreen device 32 is arranged in the annotation region 54 underneath the portion of the printable medium 52 such that a user of the fetal monitoring system can generate the freeform annotations 36 by writing on the exposed portion of the printable medium 52, which writing is captured by the underlying pressure-sensitive touchscreen device 32 and added to the digitized representation of the fetal monitoring sensor data for storage in the data storage device 28 as explained in more detail above. This has the advantage that a user, e.g. a medical professional, may generate the freeform annotations 36 in a customary manner whilst at the same time facilitating the automatic generation of the freeform annotations 36 in a digital format.

Figure 6:
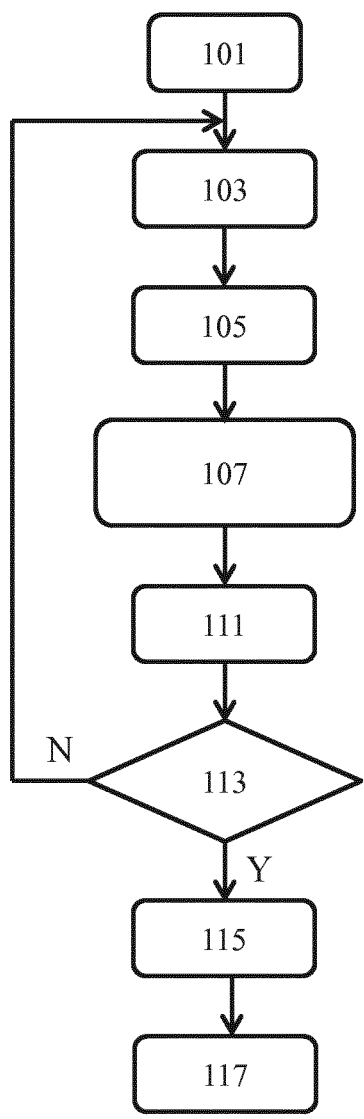
FIG. 6 depicts a flowchart of a computer-implement the method according to an embodiment of the present invention.

FIG. 6 is a flowchart of a method 100 implemented by the processor arrangement 24 of the computing device arrangement 20 in accordance with embodiments of the present invention. The method 100 starts in operation 101, in which the fetal monitoring arrangement 10 may be attached to the pregnant woman in any suitable manner as previously mentioned and switched on, such that the processor arrangement 24 receives the fetal monitoring data from the fetal monitoring arrangement 10 through the data communication module 22. The processor arrangement 24 processes the received fetal monitoring data and controls the display device 30 to display the fetal monitoring data in operation 105. In operation 107, the processor arrangement 24 receives a freeform input 36 in a region of a touchscreen device 32 from the touchscreen device 32, which freeform input 36 is used by the processor arrangement 24 in operation 111 to modify the fetal monitoring data by annotating a displayed region of the fetal monitoring data corresponding to the region of the touchscreen device in which the freeform input 36 was received with this freeform input.

In operation 113, the processor arrangement 24 checks if the fetal monitoring is to be continued. If this is the case, the method 100 reverts back to operation 103, otherwise the method 100 proceeds to operation 115 in which the processor arrangement generates an output of the modified fetal monitoring data by storing the data modified with the freeform annotations 36 in the data storage device 28 as previously explained. Alternatively, the processor arrangement 24 may store this modified fetal monitoring data in the data storage device 28 in a continuous fashion or in batches during the fetal monitoring, in which case operations 113 and 115 may be interchanged. Upon storage of the modified fetal monitoring data in the data storage device 28 and completion of the fetal monitoring, the method 100 may terminate in operation 117. The completion of the fetal monitoring may be achieved in any suitable manner, such as by initiation of a patient discharge procedure for which a dedicated button such as a push button or smart button may be used.

Figure 7:
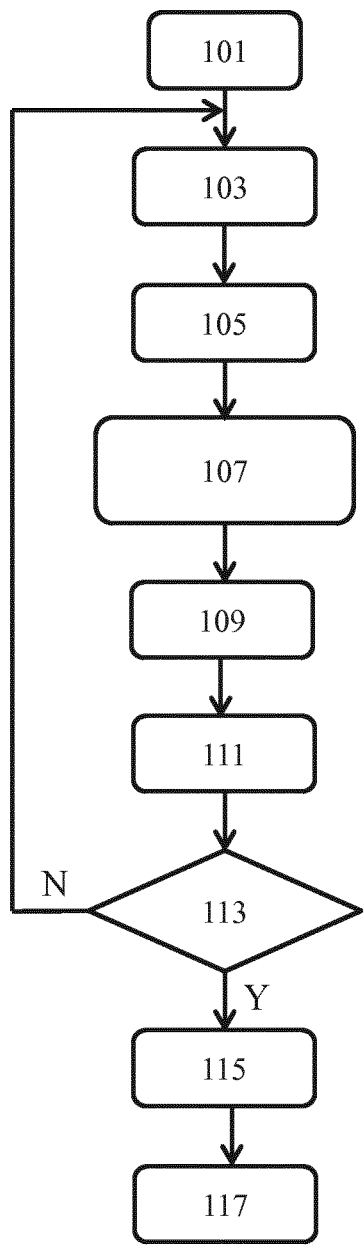
FIG. 7 depicts a flowchart of a computer-implement the method according to another embodiment of the present invention.

As previously explained, the method 100 may be modified in accordance with the flowchart depicted in FIG. 7 by labelling the freeform annotations 36 received in operation 107 with user information. To this end, the method 100 further comprises an operation 109 in which the processor arrangement 24 receives user information extracted from the RFID tag 42 with the RFID tag reader 26 from the RFID tag reader and labels the freeform annotation 36 with the thus received user information in operation 111 before proceeding to operation 113 as previously explained.

At this point, it will be further explained how freeform annotations 36 labelled with such user information may be leveraged in embodiments of the present invention. In a first example embodiment, a user may be especially interested in freeform annotations 36 generated by a particular type of user. For example, a doctor or consultant may be especially interested in freeform annotations 36 inserted into the fetal monitoring data by other doctors or consultants, by midwives, and so on. In such a scenario, the processor arrangement 24 may be arranged to deploy colour coding to the freeform annotations 36 displayed on the display device 30 such that freeform annotations 36 generated by a particular type of user are displayed in a colour associated with that the type of user, such that for example freeform annotations 36 generated by consultants or doctors are displayed in a different colour to freeform annotations 36 generated by midwives such that a user evaluating the modified fetal monitoring data including such a freeform annotations 36 can immediately recognize which type of user, e.g. which type of medical professional, was responsible for the generation of a particular freeform annotation 36 in the data. This may be achieved in any suitable manner. For example, the user information stored in the RFID tag 42 may identify the user type of the person wearing or holding the RFID tag 42, in which case the processor arrangement 24 may be programmed to recognize different types of users and associate their freeform annotations 36 with a particular colour assigned to that user type. The processor arrangement 24 may embed the thus identified colour as a metadata label of the freeform annotation 36 included in the modified fetal monitoring data or alternatively may embed user information in the freeform annotation 36 such that prior to displaying the modified fetal monitoring data including the freeform annotation 36, the label of the freeform annotation 36 is processed to determine the colour in which the freeform annotation 36 is to be displayed on the display device 30.

In another example embodiment, certain regions or locations in the fetal monitoring data may be made accessible for such freeform annotations 36 based on user type. For example, only a doctor may be allowed to annotate the initial and final parts of the fetal monitoring data, e.g. for signing off the data, such that staff not authorized to sign off the data, e.g. nursed, cannot do so.

In another example embodiment, the user information is used to determine which freeform annotations 36 are to be displayed to a particular user. For example, where a particular user attempts to retrieve previously stored fetal monitoring data modified with the freeform annotations 36 from the data storage device 28 for displaying on the display device 30, such a user may need to provide authorisation information in order to gain access to such previously stored data. This may be achieved by such a user wearing a further RFID tag 42 or using a stylus 40 including such an RFID tag 42 as previously explained, with the processor arrangement 24 being arranged to receive the user information from the further RF tag from the RF tag reader 26, which information identifies the user requesting the retrieval of the previously stored modified fetal monitoring data. The processor arrangement 24 subsequently evaluates the data from the further RF tag to establish an authorisation level of the user requesting the retrieval of previously stored modified fetal monitoring data, for example by consulting a database of users in which each authorised user is identified. The thus established authorisation level may be used by the processor arrangement 24 to only visualize those freeform annotations 36 in the retrieved fetal monitoring data that the user is allowed or authorised to see. In this manner, it for example may be prevented that nurses or midwives evaluating previously stored fetal monitoring data modified with freeform annotations 36 can read annotations by higher ranking medical professionals such as doctors or consultants. Other scenarios will be immediately apparent to the skilled person. In order to visualize such freeform annotations 36, the processor arrangement 24 may control the display device to display the retrieved modified fetal monitoring data, wherein only the freeform annotations 36 are displayed that the user requesting the retrieval of previously stored modified fetal monitoring data is authorised to see. Alternatively, where such a user requests a printout of such retrieved modified fetal monitoring data, only the freeform annotations are printed displayed that the user requesting the retrieval of previously stored modified fetal monitoring data is authorised to see.

Figure 8:
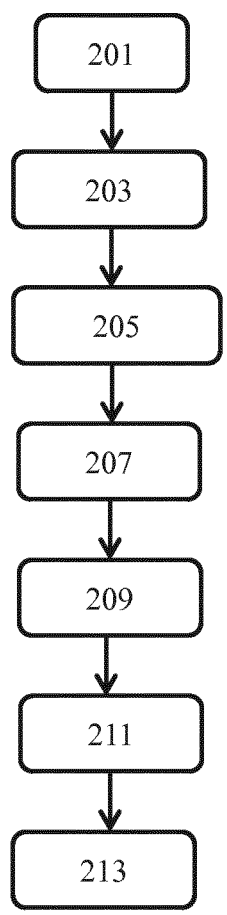
FIG. 8 depicts a flowchart of an aspect of a computer-implement the method according to yet another embodiment of the present invention.

FIG. 8 depicts a flowchart of an example embodiment of a method 200 of visualizing the freeform annotations 36 with fetal monitoring data previously stored in a data storage device 28 and retrieved therefrom as explained above. The method 200 starts in operation 201, e.g. by a user gaining access to the computing device arrangement 20 by logging on the like, after which the method proceeds to operation 203 in which the processor arrangement 34 receives a request from the user to retrieve previously stored fetal monitoring data modified with freeform annotations 36 from the data storage device 28. The processor arrangement 24 retrieves the requested data in operation 205 and receives the RFID tag information, i.e. the user information, stored in the RFID tag 42 of the user from RFID tag reader 26 in operation 207.

In operation 209, the processor arrangement 24 evaluates the user information received from the RFID tag reader 26, for example to determine the identity of the user, the type of user, e.g. the professional function or capacity of the user, an authorisation level of the user and so on, which evaluation result is used by the processor arrangement 24 to control the display device 30 (or a printing device in an alternative embodiment) to display the modified fetal monitoring data retrieved from the data storage device 28 in operation 211 in which the freeform annotations 36 in the modified fetal monitoring data are displayed in accordance with the evaluation of the user information retrieved from the RFID tag 42 associated with the user requesting the retrieval of the previously stored fetal monitoring data, which as previously explained may by way of non-limiting example include colour coding the freeform annotations 36 in accordance with the retrieved user information or displaying only those freeform annotations 36 that the user is authorised to see based on the user information retrieved from the RFID tag 42 associated with that user as explained above in more detail. Upon displaying or otherwise visualizing the retrieved modified fetal monitoring data in operation 211, the method 200 terminates in operation 213.

Although in the above embodiments the computing device arrangement comprises a RF tag reader as identification means, in other embodiments the computing arrangement can comprise a finger print reader as identification means. The finger print reader can be incorporated into the touchscreen or can be a separate device, for instance, positioned near the touchscreen device. The finger print reader is adapted to read finger print data, wherein the finger print data comprises user information, i.e. information on the identity of the user. Moreover, the finger print reader can be connected with a storage unit storing the user information with regard to the finger print data. In this embodiment the carrying of a specific RF tag by the user can be omitted, while at the same time the security of the computing device arrangement can be ensured.

The above described embodiments of the methods 100 and 200 may be realized by computer readable program instructions embodied on a computer readable storage medium having, when executed on a processor arrangement 24, cause the processor arrangement to implement the method 100 and/or 200. Any suitable computer readable storage medium may be used for this purpose, such as for example an optically readable medium such as a CD, DVD or Blu-Ray disc, a magnetically readable medium such as a hard disk, an electronic data storage device such as a memory stick or the like, and so on. The computer readable storage medium may be a medium that is accessible over a network such as the Internet, such that the computer readable program instructions may be accessed over the network. For example, the computer readable storage medium may be a network-attached storage device, a storage area network, cloud storage or the like. The computer readable storage medium may be an Internet-accessible service from which the computer readable program instructions may be obtained. In an embodiment, the computing device arrangement 20 is adapted to retrieve the computer readable program instructions from such a computer readable storage medium and to create a new computer readable storage medium by storing the retrieved computer readable program instructions in a data storage arrangement (not shown), e.g. in a memory device or the like forming part of the data storage arrangement.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A device for receiving fetal monitoring data from a fetal monitoring system, the device comprising:
    a display device configured to display the fetal monitoring data;
    a touchscreen device;
    a processor communicatively coupled to the display device and the touchscreen device, the processor configured to:
        receive the fetal monitoring data from the fetal monitoring system;
        control the display device to display the fetal monitoring data;
        receive a freeform input in a region of the touchscreen device from the touchscreen device;
        modify the fetal monitoring data by annotating a displayed region of the fetal monitoring data with the freeform input, said displayed region corresponding to the region of the touchscreen device;
        generate an output of the modified fetal monitoring data for storage in a data storage device; and
    a printer device configured to print at least some of the displayed fetal monitoring data from the fetal monitoring system on a printable medium, the printer device comprising an annotation region exposing a portion of the printable medium comprising the fetal monitoring data printed thereon, and wherein the touchscreen device is a touchscreen device arranged in the annotation region underneath said portion of the printable medium, and wherein the printable medium scrolls over the annotation region of the touchscreen device as it is printed by the printer device, and wherein the freeform input comprises a handwritten annotation drawn by a user using the user's finger or a stylus on the annotation region of the printed medium which is simultaneously detected by the touchscreen device, and wherein the device further comprises identification means communicatively coupled to the processor, wherein the processor is configured to receive identification data comprising user information identifying the user generating the freeform input from the identification means and to label at least some of said freeform annotations based on the identification data of the user generating the freeform input, and wherein the processor is further configured to control the display device to display one or more labelled freeform annotations in a visible display method indicating a user responsible for the generation of said annotation, or a type of user responsible for the generation of said annotation.

2. The device of claim 1, wherein the identification means comprises an RF (radio frequency) tag reader or a finger print reader, wherein RF tag data received from the RF tag reader and finger print data received from the finger print reader comprise identification data.

3. The device of claim 2, further comprising a plurality of styluses for generating the freeform input on the touchscreen device, each stylus comprising a RF tag programmable to contain said user identifying information.

4. The device of claim 1, wherein the processor is further configured to:

receive a user request for the retrieval of previously stored modified fetal monitoring data;

retrieve the user-requested modified fetal monitoring data from the data storage device; and control the display device to display the retrieved modified fetal monitoring data, wherein each of the labelled freeform annotations is displayed as a function of its label.

5. The device of claim 4, wherein the processor is further configured to control the display device to display each labelled freeform annotation in a color indicative of a type of the user responsible for the generation of said annotation.

6. The device of claim 4, wherein the processor is further configured to:

receive further identification data from the identification means, said further identification data identifying a user requesting the retrieval of previously stored modified fetal monitoring data;

evaluate the further identification data to establish an authorization level of the user requesting the retrieval of previously stored modified fetal monitoring data; and control the display device to display the retrieved modified fetal monitoring data, wherein only the freeform annotations labelled based on the received identification data are displayed that the user requesting the retrieval of previously stored modified fetal monitoring data is authorized to see.

7. A fetal monitoring system comprising:

a fetal monitoring sensor; and a display device configured to display the fetal monitoring data;

a touchscreen device;

a processor communicatively coupled to the display device and the touchscreen device, the processor configured to:

receive the fetal monitoring data from the fetal monitoring sensor;

control the display device to display the fetal monitoring data;

receive a freeform input in a region of the touchscreen device from the touchscreen device, wherein the freeform input comprises a handwritten annotation drawn by a user using the user's finger or a stylus;

modify the fetal monitoring data by annotating a displayed region of the fetal monitoring data with the freeform input, said displayed region corresponding to the region of the touchscreen device;

generate an output of the modified fetal monitoring data for storage in a data storage device;

identification means communicatively coupled to the processor, wherein the processor is further configured to receive identification data comprising user information identifying the user generating the freeform input from the identification means and to label at least some of said freeform annotations based on the identification data of the user generating the freeform input, and wherein labelling at least some of said freeform annotations comprises labelling one or more freeform annotations using a visible display method indicating a user responsible for the generation of said annotation, or a type of user responsible for the generation of said annotation; and a printer device configured to print at least some of the displayed fetal monitoring data from the fetal monitoring system on a printable medium, the printer device comprising an annotation region exposing a portion of the printable medium comprising the fetal monitoring data printed thereon, and wherein the touchscreen device is a touchscreen device arranged in the annotation region underneath said portion of the printable medium, and wherein the printable medium scrolls over the annotation region of the touchscreen device as it is printed by the printer device, and wherein the freeform input is provided on the annotation region of the printed medium which is simultaneously detected by the touchscreen device.

8. A computer-implemented method of annotating fetal monitoring data, the method comprising:

receiving the fetal monitoring data from a fetal monitoring system;

displaying the fetal monitoring data on a display device;

receiving a freeform input in a region of a touchscreen device from the touchscreen device, wherein the freeform input comprises a handwritten annotation drawn by a user using the user's finger or a stylus;

modifying the fetal monitoring data by annotating a displayed region of the fetal monitoring data with the freeform input, said displayed region corresponding to the region of the touchscreen device;

generating an output of the modified fetal monitoring data for storage in a data storage device;

receiving identification data comprising user information for a user generating the freeform input from an identification means;

labelling the freeform annotation based on said identification data, wherein labelling the freeform annotations comprises labelling one or more of the freeform annotations using a visible display method indicating a user responsible for the generation of said annotation, or a type of user responsible for the generation of said annotation; and printing, with a printer device, at least some of the displayed fetal monitoring data from the fetal monitoring system on a printable medium, the printer device comprising an annotation region exposing a portion of the printable medium comprising the fetal monitoring data printed thereon, and wherein the touchscreen device is a touchscreen device arranged in the annotation region underneath said portion of the printable medium, and wherein the printable medium scrolls over the annotation region of the touchscreen device as it is printed by the printer device, and wherein the freeform input is provided on the annotation region of the printed medium which is simultaneously detected by the touchscreen device.

9. The computer-implemented method of claim 8, further comprising:

receiving a user request for the retrieval of previously stored modified fetal monitoring data;

retrieving the user-requested modified fetal monitoring data from the data storage device; and controlling the display device to display the retrieved modified fetal monitoring data, wherein each of the freeform annotations labelled based on the received identification data is displayed as a function of its label.

10. The computer-implemented method of claim 9, wherein displaying each of the freeform annotations labelled based on the received identification data as a function of its label comprises controlling the display device to display each labelled freeform annotation in a color indicative of a type of the user responsible for the generation of said annotation.

11. The computer-implemented method of claim 9, further comprising:
- receiving further identification data from the identification means, said further identification data identifying a user requesting the retrieval of previously stored modified fetal monitoring data;
- evaluating the further identification data to establish an authorization level of the user requesting the retrieval of previously stored modified fetal monitoring data; and
- wherein controlling the display device to display the retrieved modified fetal monitoring data comprises displaying only the labelled annotations that the user requesting the retrieval of previously stored modified fetal monitoring data is authorized to see.

12. A non-transitory computer readable medium comprising computer readable program instructions embodied therewith for, when executed on a processor causes the processor to perform the steps comprising:
- receiving the fetal monitoring data from a fetal monitoring system;
- displaying the fetal monitoring data on a display device;
- receiving a freeform input in a region of a touchscreen device from the touchscreen device, wherein the freeform input comprises a handwritten annotation drawn by a user using the user's finger or a stylus;
- modifying the fetal monitoring data by annotating a displayed region of the fetal monitoring data with the freeform input, said displayed region corresponding to the region of the touchscreen device;
- generating an output of the modified fetal monitoring data for storage in a data storage device;
- receiving identification data comprising user information for a user generating the freeform input from an identification means; and
- labelling the freeform annotation based on said identification data, wherein labelling the freeform annotations comprises labelling one or more of the freeform annotations using a visible display method indicating a user responsible for the generation of said annotation, or a type of user responsible for the generation of said annotation; and
- printing, with a printer device, at least some of the displayed fetal monitoring data from the fetal monitoring system on a printable medium, the printer device comprising an annotation region exposing a portion of the printable medium comprising the fetal monitoring data printed thereon, and wherein the touchscreen device is a touchscreen device arranged in the annotation region underneath said portion of the printable medium, and wherein the printable medium scrolls over the annotation region of the touchscreen device as it is printed by the printer device, and wherein the freeform input is provided on the annotation region of the printed medium which is simultaneously detected by the touchscreen device.

* * * * *